United States Patent [19]

Berg et al.

[11] Patent Number: 4,814,165

[45] Date of Patent: Mar. 21, 1989

[54] EMULSIFIED HYDRATED STICK PRODUCT

[75] Inventors: Richard D. Berg, Port Jervis, N.Y.; John H. Murphy, Germantown, Tenn.; Stephen Casperson, Norwalk, Conn.

[73] Assignee: Kolmar Laboratories Inc., Port Jervis, N.Y.

[21] Appl. No.: 21,192

[22] Filed: Mar. 3, 1987

[51] Int. Cl.$^4$ .................. A61K 7/021; A61K 7/031; A61K 7/38; A61K 7/40

[52] U.S. Cl. ........................ 424/63; 424/DIG. 5; 424/59; 424/60; 424/64; 514/847; 514/873

[58] Field of Search ................ 424/65, 66, 68, 63

[56] References Cited

U.S. PATENT DOCUMENTS

| | | | |
|---|---|---|---|
| 4,126,679 | 11/1978 | Davey et al. | 424/65 |
| 4,166,108 | 8/1979 | Brown et al. | 424/23 |
| 4,280,994 | 7/1981 | Turney | 424/65 |
| 4,331,653 | 5/1982 | Brown | 424/28 |
| 4,473,582 | 9/1984 | Greene | 424/305 |
| 4,478,853 | 10/1984 | Chaussee | 424/358 |
| 4,511,554 | 4/1985 | Geria et al. | 424/65 |
| 4,556,554 | 12/1985 | Calvo | 424/70 |

FOREIGN PATENT DOCUMENTS 0117070  8/1984  European Pat. Off. ............ 424/65

*Primary Examiner*—Dale R. Ore
*Attorney, Agent, or Firm*—Andrus, Sceales, Starke & Sawall

[57] ABSTRACT

A solid hydrated stick for topical application containing emulsified water soluble ingredients and volatile emollients. The stick is a solid emulsion comprising by weight from 15% to 40% of a cyclic silicone, 2% to 15% of an oil, 2% to 20% of a wax, 2% to 7% of polyethylene glycol sorbitan beeswax, 10% to 40% water, and 0.1% to 40% of a cosmetically acceptable functional ingredient. The polyethylene glycol sorbitan beeswax acts as an emulsifier and contributes to the rigidity of the stick, while the silicone serves as an emollient to impart a smooth, buttery feel when the composition is applied to the skin.

10 Claims, No Drawings

EMULSIFIED HYDRATED STICK PRODUCT

BACKGROUND OF THE INVENTION

Historically, solid stick products have been used in the cosmetic and pharmaceutical industries for their convenience and ease of application over creams or lotions. The conventional solid stick is anhydrous and is composed largely of oils and waxes. The waxes are needed to achieve a rigid structure to permit the stick to stand upright and the oils are required to plasticize the waxes to allow mass release to the skin. Coloring agents or other active ingredients are incorporated in the oil and wax base.

Anhydrous sticks have the disadvantage of applying large quantities of oil and wax to the skin, thus producing a heavy lardy feel to the skin. This is a negative feeling but one previously thought necessary because of the waxy ingredients needed to produce a rigid stick.

Recently, cyclic or volatile silicones have been utilized as emollients in cosmetic or pharmaceutical products. The silicones have been used in place of the conventional plasticizing oils and after application to the skin, the silicone evaporates leaving a wax/color or active ingredient matrix on the skin. The evaporative effect is less occlusive than the conventional oil/wax matrix and thus is more comfortable to the user. While the use of silicones as an ermollient represents an improvement over earlier technology, the final feed on the skin is still heavy and waxy after the volatile silicone evaporates from the skin.

SUMMARY OF THE INVENTION

The invention is directed to a solid stick for topical application that contains emulsified water soluble ingredients and volatile emollients. The stick is a solid emulsion comprising by weight from 15% to 40% of a volatile cyclic silicone, 2% to 15% of oils, 2% to 20% of waxes, 2% to 7% of polyethylene glycol sorbitan beeswax, 10% to 40% water and from 0.1% to 40% of a cosmetically acceptable functional ingredients.

The polyethylene glycol sorbitan beeswax acts to emulsify the oils, waxes and emollient in the water base and also contributes to the rigidity of the stick.

The cyclic silicone serves as an emollient and evaporates along with the water when the composition is applied to the skin to provide a smooth buttery feel, as opposed to a heavy, waxy feel for the conventional anhydrous stick.

As the water soluble functional ingredients, such as colorants or active ingredients, are delivered in solution to the skin, they are applied in a diluted non-irritating form ready to perform their function when delivered.

The stick composition of the invention can be used to provide a wide variety of cosmetic and pharmaceutical products.

Other objects and advantages will appear in the course of the following description.

DESCRIPTION OF THE PREFERRED EMBODIMENT

The invention is directed to a solid stick composition for topical application which contains emulsified water soluble ingredients and volatile emollients. In general, the stick has the following composition in weight percent.

| | |
|---|---|
| Volatile cyclic silicone | 15–40% |
| Oils | 2–15% |
| Waxes | 2–20% |
| Polyethylene glycol sorbitan beeswax | 2–7% |
| Water | 10–40% |
| Functional ingredients | 0.1–40% |

The volatile silicone is a liquid at room temperature and preferably takes the form of a siloxane composed primarily of two cyclic components: D4 cyclomethicone and D5 cyclomethicone. The D5 component represents the majority with the D4 being a minor constituent. Chemically D4 cyclomethicone may be symbolically written as:

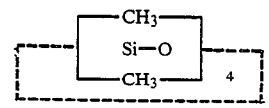

and D5 cyclomethicone may be symbolically written as:

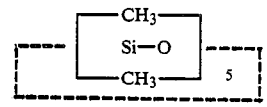

The silicone acts as an emollient during application to the skin, leaving an emulsified matrix of waxes and colorants or active ingredients on the skin. Since the waxes are emulsified, and both the silicone and the water evaporate after application, a smooth light buttery feel is imparted to the skin as opposed to the heavy, waxy or lardy feel associated with a conventional anhydrous stick.

The oils can take the form of any oils normally employed in cosmetic or pharmaceutical products and may be selected from mineral oil, corn oil, soybean oil, apricot kernel oil, coconut oil, clove oil, lemon oil, olive oil, sunflower seed oil, jojoba oil, sesame oil, peanut oil, safflower oil, grapeseed oil, castor oil, cotton seed oil, avocado oil, almond oil, wheat germ oil, oil of orchids and rice bran oil.

The waxes are common types used in cosmetic and pharmaceutical products such as ceresin wax, castor wax, carnauba wax, paraffin was, candelilla wax, bees wax, ozokerite, microcrystalline wax, bayberry wax, Japan wax, rice bran wax, spermaceti wax. In addition, fatty acid alcohols containing from 12 to 22 carbon atoms, such as straight alcohol, lauryl alcohol, and the like, can also be used as the wax component.

The polyethylene glycol sorbitan beeseax is an ethoxylated sorbitol derivative of beeswax containing various moles of ethylene oxide. For example, Atlas G-1726 (ICI Americas Inc.) is an ethoxylated sorbitol derivative of beeswax with an average of 20 moles of ethylene oxide. Other derivatives such as those containing an average of 6 or 8 moles of ethylene oxide can also be utilized.

The term "functional ingredients" as used in the description and claims is intended to cover active ingredients, colorants and other additives to the composition. The functional ingredients can take the form of colorants such as guanine crystals, carmine, bismuth oxychloride, mica, iron oxides, titanium dioxide, manganese violet, ultramarine blue, ultramarine pink, ultramarine violet, ultramarine rose, chromium hydroxide green, chromium oxide green, bronze powder, aluminum powder, ferric ferrocyanide, ferric ammonium ferrocyanide, and D & C organic pigments; anti-perspirants such as aluminum chlorohydrate, or aluminum zirconium tetrachlorohydrexyglycine; bacteriacides such as mercuochrome; skin lightening agents such as hydroquinone; auxilliary emulsifiers or texturizers such as methyl glycose dioleate; suspending agents such as magnesium aluminum silicate; preservatives such as methyl paraben; and other functional materials commonly used in topical products such as panthenol, lanolin, collagen, aloe vera, honey, ginseng extract, sodium thioglycolate, fragrances, 2-pyrrolidone-5-carboxylic acid, vitamins, chammomile extract, witch hazel extract, lemon juice, comfrey extract, rosehips, mint extract, hayflower extract, glycerin, 1,3 butylene glycol, propylene glycol, sodium lauryl sulfoactetate and polyamino sugar condensate (and) urea.

To prepare the stick composition of the invention, the silicone, oils, waxes and the emulsifier are heated to a temperature generally in the range of 60° to 80° C. to provide a liquid mixture. Water, along with the water soluble functional ingredients, are admixed with the liquid mixture and the combination is agitated or homogenized at a temperature of 60° to 80° C. to provide the emulsion. The emulsion is then poured by gravity either directly into the final package to form the solidified stick product, or into molds to form sticks which are subsequently transferred to the final package.

The stick composition of the invention contains a substantially lesser amount of waxes and oils than a conventional anhydrous stick. The volatile silicone acts as an emollient during application leaving an emulsified matrix of waxes and oils along with functional ingredients on the skin. After application, the silicone as well as the water will evaporate from the skin and the evaporative affect imparts a smooth, light feel to the skin as opposed to the heavy, waxy or lardy feel associated with the conventional anhydrous stick.

As a further advantage, the colors have a deeper or more intensive affect on the skin since there is a lesser wax matrix to interfere with their perception.

As large quantities of oil are not required to affect mass release to the skin, the product will wear longer on the skin since oils present cause creasing of color from the skin.

A further advantage is that the water soluble functional ingredients are delivered in solution to the skin. In addition to achieving faster results on the skin, the functional ingredients are less irritating since they are already diluted in solution and do not have to be solubilized by the skins ingredients.

The following examples illustrate the solid stick composition of the invention.

| I. Blusher Stick | |
|---|---|
| Cyclomethicone | 23.90% |
| Stearyl alcohol | 16.00 |
| PEG-20 sorbitan beeswax | 2.00 |
| Sesame oil | 2.00 |
| Methyl glucose dioleate | 1.00 |
| 1% Aq. dispersion magnesium aluminum silicate | 30.00 |
| Color blend | 25.00 |
| | 100.00% |

| II. Cosmetic | |
|---|---|
| Cyclomethicone | 34.55% |
| Stearyl alcohol | 18.67 |
| PEG-20 sorbitan beeswax | 2.67 |
| Sesame Oil | 2.67 |
| Methyl glucose dioleate | 1.34 |
| Deionized water | 33.60 |
| 5-hydroxy-6-methyl-3,4-pyridinedimethyanol hydrochloride | 5.00 |
| (2,5-dioxo-4-imidazolidinyl) urea | .50 |
| | 100.00% |

| III. Sunscreen Stick: | |
|---|---|
| Octyl dimethyl PABA | 8.00% |
| Cyclomethicone | 35.65 |
| Stearyl alcohol | 18.67 |
| PEG-20 sorbitan beeswax | 2.67 |
| Sesame oil | 2.67 |
| Methyl glucose dioleate | 1.34 |
| Deionized water | 30.00 |
| | 100.00% |

| IV. Antiperspirant Stick: | |
|---|---|
| Magnesium aluminum silicate 5% dispersion Aq. | 36.50% |
| Aluminum chlorohydrate | 18.00 |
| Cyclomethicone | 21.50 |
| Stearyl alcohol | 18.00 |
| PEG-20 sorbitan beeswax | 3.00 |
| Sesame oil | 2.00 |
| Methyl glucose dioleate | 1.00 |
| | 100.00% |

| V. Sunscreen with aloe stick: | |
|---|---|
| Octyl dimethyl PABA | 8.00% |
| Cyclomethicone | 36.15 |
| Stearyl alcohol | 18.67 |
| PEG-20 sorbitan beeswax | 2.67 |
| Sesame oil | 2.67 |
| Methyl glucose dioleate | 1.34 |
| Deionized water | 24.50 |
| Aloe | 5.00 |
| | 100.00% |

| VI. Blusher Stick: | |
|---|---|
| Cyclomethicone | 21.50 |
| Stearyl Alcohol | 16.00 |
| PEG-20 Sorbitan Beeswax | 5.00 |
| Sesame Oil | 5.00 |
| Methyl glucose dioleate | 1.00 |
| Propylparaben | 0.20 |
| 1% Aq. dispersion magnesium aluminum silicate | 26.00 |
| Methylparaben | 0.30 |
| Color Blend | 25.00 |
| | 100.00% |

| VII. Blusher Stick | |
|---|---|
| Cyclomethicone | 24.50 |
| Stearyl alcohol | 14.00 |
| PEG-20 Sorbitan beeswax | 7.00 |
| Sesame oil | 7.00 |
| Methyl glucose | 1.00 |
| Propylparaben | 0.20 |
| 1% Aq. dispersion magnesium aluminum silicate | 26.00 |
| Methylparaben | 0.30 |
| Color blend | 20.00 |
| | 100.00% |

Various modes of carrying out the invention are contemplated as being within the scope of the following claims particularly pointing out and distinctly claiming the subject matter which is regarded as the invention.

We claim:

1. A solid emulsified stick composition for topical application, comprising by weight from 15% to 40% of a cyclic volatile silicone, 2% to 15% of a cosmetically acceptable wax, 2% to 7% of polyethylene glycol sorbitan beeswax, 10% to 40% water and 0.1% to 40% of a cosmetically acceptable functional ingredient.

2. The stick composition of claim 1, wherein said wax is a fatty acid alcohol containing from 12 to 22 carbon atoms.

3. The stick composition of claim 2, wherein said fatty alcohol is stearyl alcohol.

4. The stick composition of claim 1, wherein said functional ingredient comprises a colorant.

5. The stick composition of claim 1, wherein said functional ingredient comprises an antiperspirant.

6. The stick composition of claim 1, wherein said silicone is cyclomethicone.

7. A solid emulsified cosmetic stick, consisting essentially of by weight from 15% to 40% of a cyclic volatile silicone, 2% to 15% of a cosmetically acceptable oil, 2% to 20% of a cosmetically acceptable wax, 2% to 7% of polyethylene glycol soribtan beeswax, 10% to 40% water, and 0.1% to 40% of a water soluble functional ingredient.

8. The stick composition of claim 7, wherein said functional ingredient comprises a colorant.

9. A solid emulsified cosmetic stick, comprising by weight from 15% to 40% of a cyclomethicone, 2% to 5% of a cosmetic oil, 2% to 20% of a cosmetic wax, 2% to 7% of polyethylene glycol sorbitan beeswax, 10% to 40% water, and 0.1% to 40% of a cosmetic colorant.

10. A solid emulsified stick composition for topical application, consisting essentially of by weight from 15% to 40% of cyclomethicone, 2% to 15% of a cosmetically acceptable oil, 2% to 20% of a cosmetically acceptable wax, 2% to 7% of polyethylene glycolsorbitan beeswax, 10% to 40% water, and 0.1% to 40% of a cosmetically acceptable functional ingredient selected from the group consisting of active ingredients, colorants and additives.

* * * * *

UNITED STATES PATENT AND TRADEMARK OFFICE
CERTIFICATE OF CORRECTION

PATENT NO. : 4,814,165
DATED : March 21, 1989
INVENTOR(S) : RICHARD D. BERG ET AL It is certified that error appears in the above-identified patent and that said Letters Patent is hereby corrected as shown below:

Col. 4, Line 66, CLAIM 1, After "acceptable" insert ---oil, 2% to 20% of a cosmetically acceptable---

Signed and Sealed this

Sixteenth Day of January, 1990

Attest:

JEFFREY M. SAMUELS

Attesting Officer

Acting Commissioner of Patents and Trademarks